(12) United States Patent
Järverud et al.

(10) Patent No.: US 9,114,263 B2
(45) Date of Patent: *Aug. 25, 2015

(54) METHOD, IMPLANTABLE MEDICAL DEVICE, AND SYSTEM FOR DETERMINING THE CONDITION OF A HEART VALVE

(75) Inventors: Karin Järverud, Solna (SE); Andreas Blomovist, Spånga (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 1064 days.

This patent is subject to a terminal disclaimer.

(21) Appl. No.: 13/131,824

(22) PCT Filed: Nov. 28, 2008

(86) PCT No.: PCT/SE2008/000671
§ 371 (c)(1),
(2), (4) Date: May 27, 2011

(87) PCT Pub. No.: WO2010/062224
PCT Pub. Date: Jun. 3, 2010

(65) Prior Publication Data
US 2011/0230746 A1 Sep. 22, 2011

(51) Int. Cl.
| A61B 5/02 | (2006.01) |
| A61N 1/362 | (2006.01) |
| A61N 1/365 | (2006.01) |
| A61N 1/368 | (2006.01) |
| A61N 1/37 | (2006.01) |

(52) U.S. Cl.
CPC .............. *A61N 1/3627* (2013.01); *A61N 1/368* (2013.01); *A61N 1/36521* (2013.01); *A61N 1/3702* (2013.01); *A61N 1/3682* (2013.01); *A61N 1/3684* (2013.01)

(58) Field of Classification Search
CPC .. A61B 5/0452; A61B 5/0006; A61B 5/0002; A61B 5/0428; A61N 1/3962; A61N 1/368; A61N 1/3627
USPC .............................. 607/9, 4, 17; 600/508, 515
See application file for complete search history.

(56) References Cited

U.S. PATENT DOCUMENTS

| 5,427,112 A | 6/1995 | Noren et al. |
| 5,556,419 A | 9/1996 | Järverud et al. |
| 5,713,933 A | 2/1998 | Condie et al. |
| 6,070,100 A | 5/2000 | Bakels et al. |
| 6,289,244 B1 | 9/2001 | Conley et al. |
| 2007/0191901 A1* | 8/2007 | Schecter ........................ 607/17 |
| 2008/0091244 A1 | 4/2008 | Richardson |

* cited by examiner

*Primary Examiner* — Catherine Voorhees
*Assistant Examiner* — Roland Dinga

(57) ABSTRACT

An implantable medical device has an impedance processor for determining atrial impedance data reflective of the cardiogenic impedance of an atrium of a heart during diastole and/or systole of heart cycle. Ventricular impedance data reflective of the cardiogenic impedance of a ventricle during diastole and/or systole are also determined. The determined impedance data are processed by a representation processor for estimating a diastolic and/or a systolic atrial impedance representation and a diastolic and/or a systolic ventricular impedance representation. A condition processor determines the presence of any heart valve malfunction, such as valve regurgitation and/or stenosis, of at least one heart valve based on the estimated atrial and ventricular impedance representations.

8 Claims, 8 Drawing Sheets

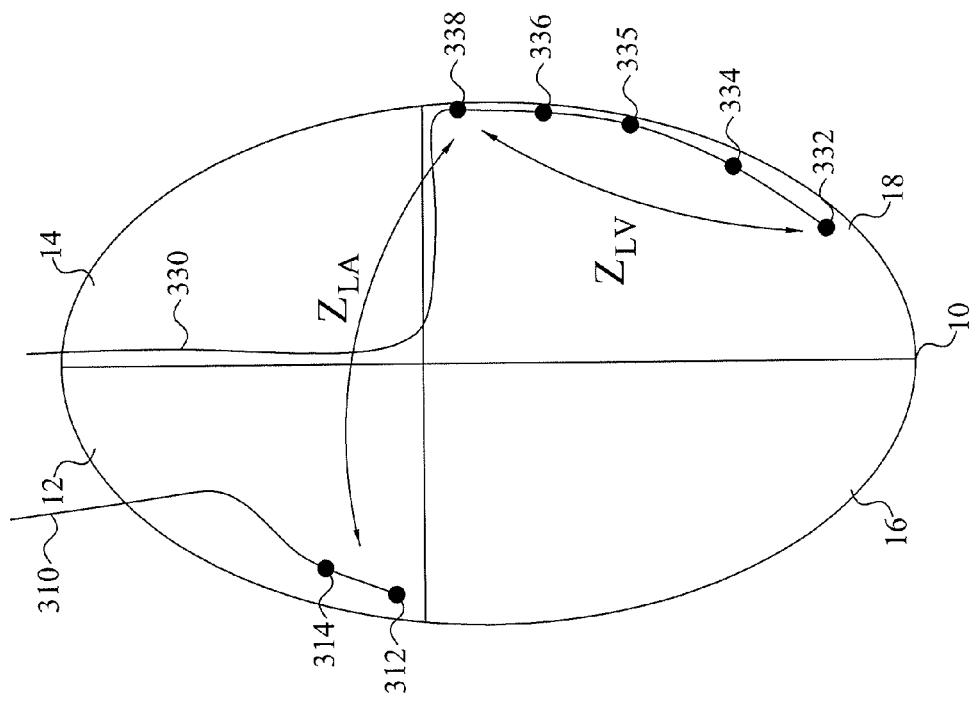
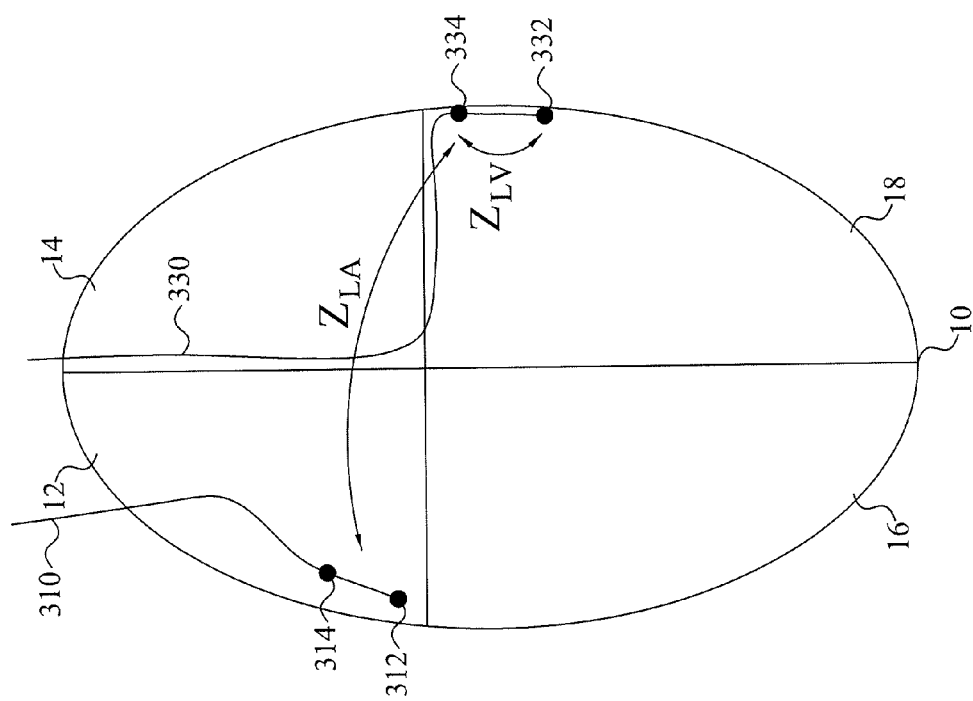
Fig. 3B
Fig. 3A

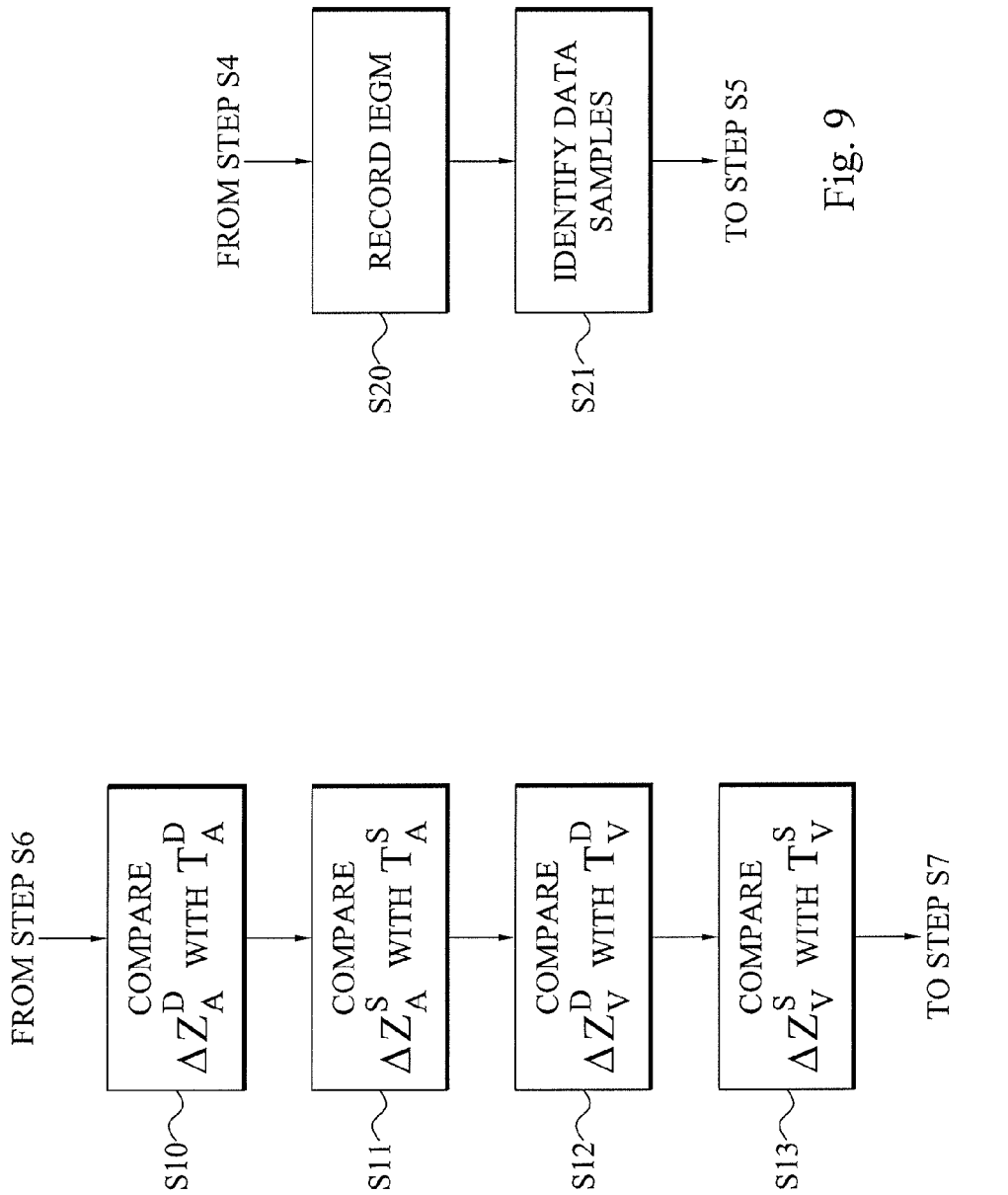

METHOD, IMPLANTABLE MEDICAL DEVICE, AND SYSTEM FOR DETERMINING THE CONDITION OF A HEART VALVE

BACKGROUND OF THE INVENTION

1. Field of the Invention

The present invention generally relates to valve condition determination, and in particular to devices and methods for determining and monitoring the condition and operation of heart valves.

2. Description of the Prior Art

The human heart comprises four heart valves controlling the flow of blood from the atriums to the ventricles and from the ventricles further on into the pulmonary or systemic circulation system. The operation of the heart valves is critical for the well-being of the subject and any valve malfunctions may lead to severe and possibly life-threatening conditions.

Generally, blood flowing incorrectly backwards through a heart valve, i.e. regurgitation, is either a primary valve related problem that might cause acute heart failure or is a secondary problem in heart failure patients. If it is a primary valve related problem, i.e. the valve has ruptured or has been damaged, e.g. through infection, valve surgery is typically employed, where the damaged valve is repaired or replaced with a new artificial valve. Any heart failure will then often resolve automatically once the valve function has been restored.

If it is a secondary problem in heart failure patients, the main source for regurgitation is probably caused by the dilated state of the heart, making it difficult for the valve to close tightly. In this latter case, monitoring valve condition and status may serve as a valuable tool to monitor heart failure.

Another common heart valve problem is valve stenosis, where the valve kinetics are disturbed making it difficult to close properly or open sufficiently.

There is therefore a need for a tool of monitoring heart valve function in order to detect any deleterious heart valve effects and/or detect primary medical conditions manifesting in change in heart valve operation.

US 2007/0191901 discloses a cardiac resynchronization therapy (CRT) device that is being programmed based on various impedance-related parameters. Multi-vector impedance signals associated with a dynamic intracardiac impedance are acquired and related to specific time frames of the cardiac cycle to derive indices representative of systolic and diastolic cardiac performance. The impedance signals are further adjusted by static impedance signals associated with pulmonary impedance as to derive composite indices representative of cardiac performance and pulmonary vascular congestion.

US 2007/0191901 also discusses that aortic valve stenosis can be detected using an aortic valve function:

$$f = \frac{1}{T_{AVO} - \frac{T_z}{\frac{dZ}{dt}}}$$

where $T_{AVO}$ denotes the time of aortic valve opening, $T_z$ denotes the onset time of positive impedance slope and $\frac{dZ}{dt}$ is the first derivative of the impedance signal and is included to account for cardiac output. A similar equation can be used for assessment of aortic valve regurgitation using delays in time to aortic valve closure from the onset of aortic valve opening or from time of peak impedance.

SUMMARY OF THE INVENTION

The prior art technique disclosed in US 2007/0191901 requires the identification of the opening and closing time of the aortic valve. These exact times may be difficult to identify in the impedance data, thereby needing additional sensor equipment, such as recording of echocardiograms, in order to identify the required times. The present embodiments overcome this and other problems with the prior art technique.

It is an object of the present invention to provide a determination of heart valve conditions.

It is another object of the invention to provide an implantable medical device capable of monitoring and determining heart valve conditions in a subject.

The above objects are achieved in accordance with the invention by an implantable medical device connectable to multiple cardiac leads having lead electrodes. Electric signals are applied, using the lead electrodes, over at least a portion of the left and/or right atrium of the heart and over at least a portion of the left and/or right ventricle of the heart. Resulting electric signals are collected from the atrium and ventricle using the lead electrodes. The electric signals are processed by an impedance processor for determining atrial impedance data and ventricular impedance data. The atrial impedance data are representative of the cardiogenic impedance of the left and/or right atrium during diastole and/or systole of at least one heart cycle. The ventricular impedance data are correspondingly representative of the cardiogenic impedance of the left and/or right ventricle during diastole and/or systole of the at least one heart cycle.

A representation processor is implemented for estimating at least one atrial impedance representation, such as a diastolic, atrial impedance representation and/or a systolic, atrial impedance representation, based on the determined atrial impedance data. The representation processor also estimates at least one ventricular impedance representation, preferably a diastolic, ventricular impedance representation and/or a systolic, ventricular impedance representation, from the ventricular impedance data.

The implantable medical device has a condition processor determining a condition of a heart valve in the heart based on the estimated atrial and ventricular impedance representations. The condition processor concludes that the heart valve is operating correctly, i.e. normal condition, or determines the presence of a valve malfunction, such as valve regurgitation or stenosis, based on the impedance representations.

Depending on which side of the heart the impedance measurements are performed and whether the atrial and ventricular impedance representations are estimated for the diastolic phase, the systolic phase or both the diastolic and systolic phase, the implantable medical device can determine the presence of:

mitral valve regurgitation—significant change in systolic, left atrial impedance representation but no significant change in systolic, left ventricular impedance representation;

mitral valve stenosis—significant changes in both diastolic, left atrial and diastolic, left ventricular impedance representations;

aortic valve regurgitation—significant change in diastolic, left ventricular impedance representation but no significant change in diastolic, left atrial impedance representation; and aortic valve stenosis—significant change in systolic, left ventricular impedance representation but no significant change in systolic, left atrial impedance representation.

The corresponding regurgitation and stenosis conditions can also be determined for the tricuspid valve and the pulmonary valve by instead using diastolic/systolic right atrial/ventricular impedance representations.

Embodiments Offer the Following Advantages:

Allows heart valve condition determination and monitoring without the usage of any extra, dedicated sensor equipment; and Can be used for monitoring any of the four heart valves or a combination of at least two heart valves.

BRIEF DESCRIPTION OF THE DRAWINGS

FIGS. 3A-3D illustrate lead configurations that can be used for determining atrial and ventricular impedances according to different embodiments.

FIG. 8 is a flow diagram illustrating additional, optional steps of the determining method in FIG. 7.

FIG. 9 is a flow diagram illustrating additional, optional steps of the determining method in FIG. 7.

DESCRIPTION OF THE PREFERRED EMBODIMENTS

Figure 1:
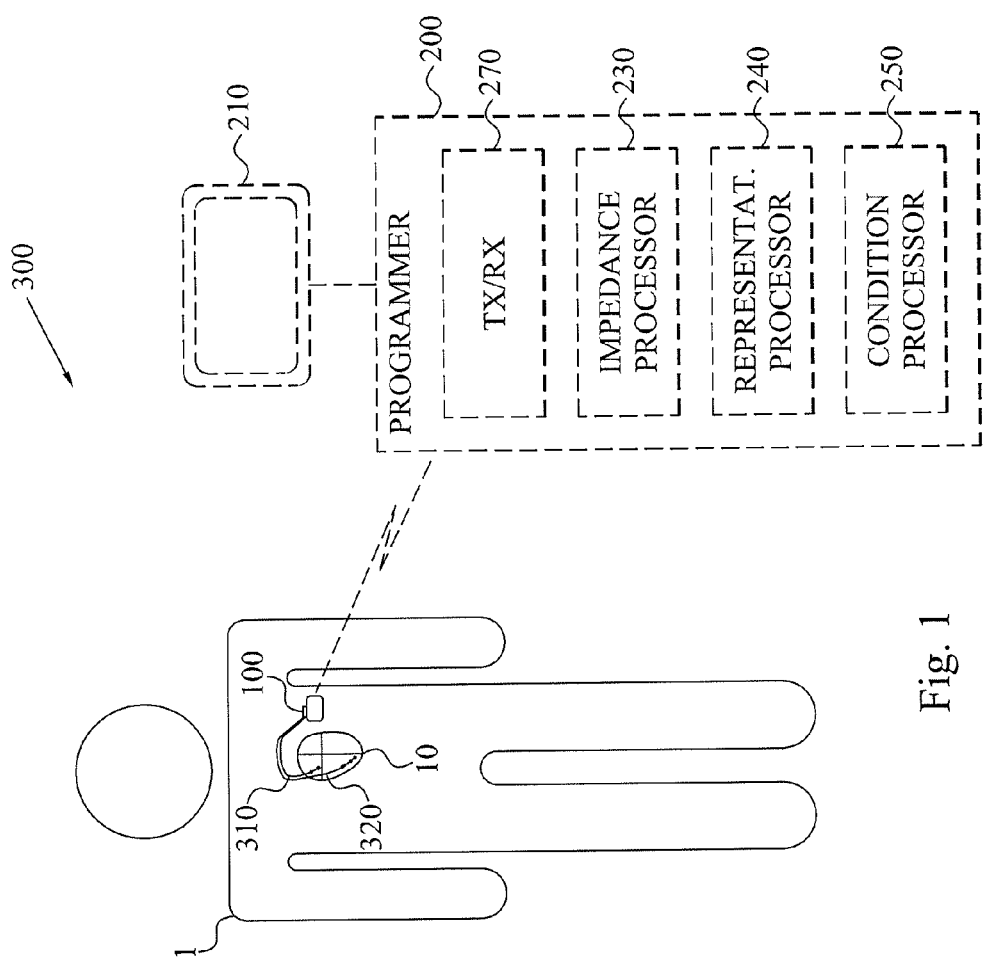
FIG. 1 is a schematic overview of a human subject having an implantable medical device according to an embodiment and an indicated external communication device.

Throughout the drawings, the same reference characters will be used for corresponding or similar elements.

The embodiments generally relate to devices and methods for monitoring and determining the condition of a heart valve of a heart in an animal subject, preferably mammalian subject and more preferably a human subject.

Figure 6:
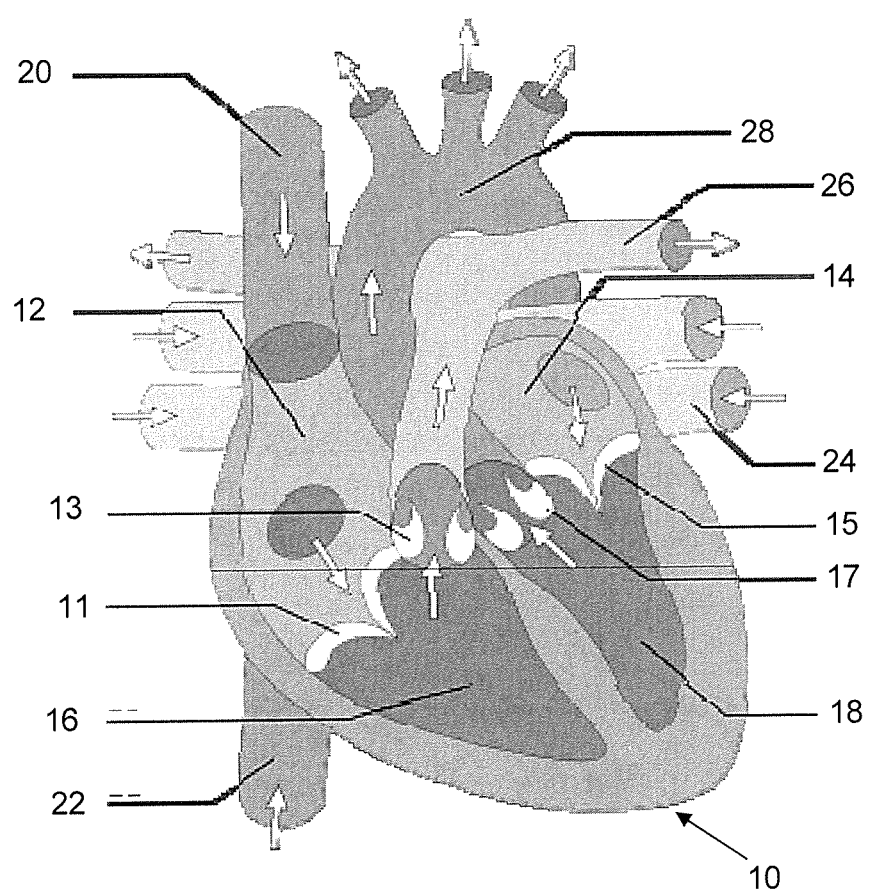
FIG. 6 is a schematic illustration of a heart with connecting main arteries and veins.

As is illustrated in FIG. 6, the human heart 10 has four heart valves 11, 13, 15, 17. Blood from the systemic circulation system enters the right atrium 12 by the superior vena cava 20 and the interior vena cava 22. A first valve, the tricuspid valve 11, regulates the flow of blood from the right atrium 12 into the right ventricle 16. The oxygen depleted blood is pumped by the contractile action of the right ventricle through the pulmonary valve 13 to the lungs via the pulmonary artery 26.

Correspondingly, on the left side of the heart 10 blood enters the left atrium 14 from the pulmonary vein 24. The blood flow from the left atrium 14 through the mitral valve 15, also denoted bicuspid valve, into the left ventricle 18. The oxygen rich blood leaves the left ventricle through the aortic valve 17 and enters the aorta 28.

The operation of these four heart valves 11, 13, 15, 17 is critical for the efficient pumping of the blood through the pulmonary and systemic circulation systems and the well-being of the subject. Medical conditions and malfunctions can effect these valves 11, 13, 15, 17 and thereby the operation of the heart 10 as whole.

For instance, medical conditions can cause a leakage of blood backwards through a heart valve, i.e. regurgitation. Valve regurgitation may in turn be due to a primary valve problem, such as a valve rupture, which may occur due to a localized heart infarct in the area around the muscle anchoring the chordae tendineae attached to the valves, or a valve damage through an infection. Also secondary problems, such as a dilation of the heart in heart failure patients, may negatively affect the valves leading to regurgitation.

Another type of medical condition that can affect the valves is stenosis. In stenosis the valves become stiffer and its kinetics is disturbed causing them not to open sufficiently.

The present invention is an efficient technique for monitoring the operation of the heart valves and determining whether a negative medical condition has occurred to a valve or if there is a worsening of a previously determined medical condition. The valve condition monitoring and determination can furthermore be conducted by an implantable medical device (IMD) having cardiac leads but does not require any dedicated heart valve sensors or other equipment. In clear contrast, traditional cardiac leads having electrodes attached to or positioned close to the heart can be used for generating data that is processed by the IMD for the purpose of the valve condition monitoring and determination.

As is further described herein, embodiments can be used for monitoring and determining the condition of one of the four heart valves. Alternatively, multiple heart valves and potentially all four valves can be monitored depending on the number of cardiac leads used and their implantation sites.

FIG. 1 is a schematic overview of a human patient 1 having an IMD 100 as taught herein. In the figure, the IMD 100 is illustrated as a device that monitors and/or provides therapy to the heart 10 of the patient 1, such as a pacemaker, cardiac defibrillator or cardioverter. The IMD 100 is, in operation, connected to one or more, two in the figure, cardiac leads 310, 320 inserted into different heart chambers, the right atrium and the right ventricle in the figure. The present invention is though not limited to right chamber leads 310, 320 but can also be used in connection with leads positioned in the left atrium or ventricle of the heart 10. Actually, also non-endocardial leads, including epicardial leads can also be used.

The patient 1 illustrated in FIG. 1 is a human patient 1. However, the present invention is not limited thereto, but can also be applied to IMDs 100 implanted in other animals, in particular other mammals.

FIG. 1 also illustrates an external programmer or clinician's workstation 200 that can communicate with the IMD 100. As is well known in the art, such a programmer 200 can be employed for transmitting IMD programming commands, using an included transmitter 270, causing a reprogramming of different operation parameters and modes of the IMD 100. Furthermore, the IMD 100 can upload diagnostic data descriptive of different medical parameters or device operation parameters collected by the IMD 100 to a receiver 270 of the programmer 200. Such uploaded data may optionally be further processed in the programmer 200 before display to a clinician on a connected display screen 210. In the light of the present disclosure, such uploaded data can include the valve condition information determined according to embodiments and other data relating to heart valve conditions.

Figure 2:
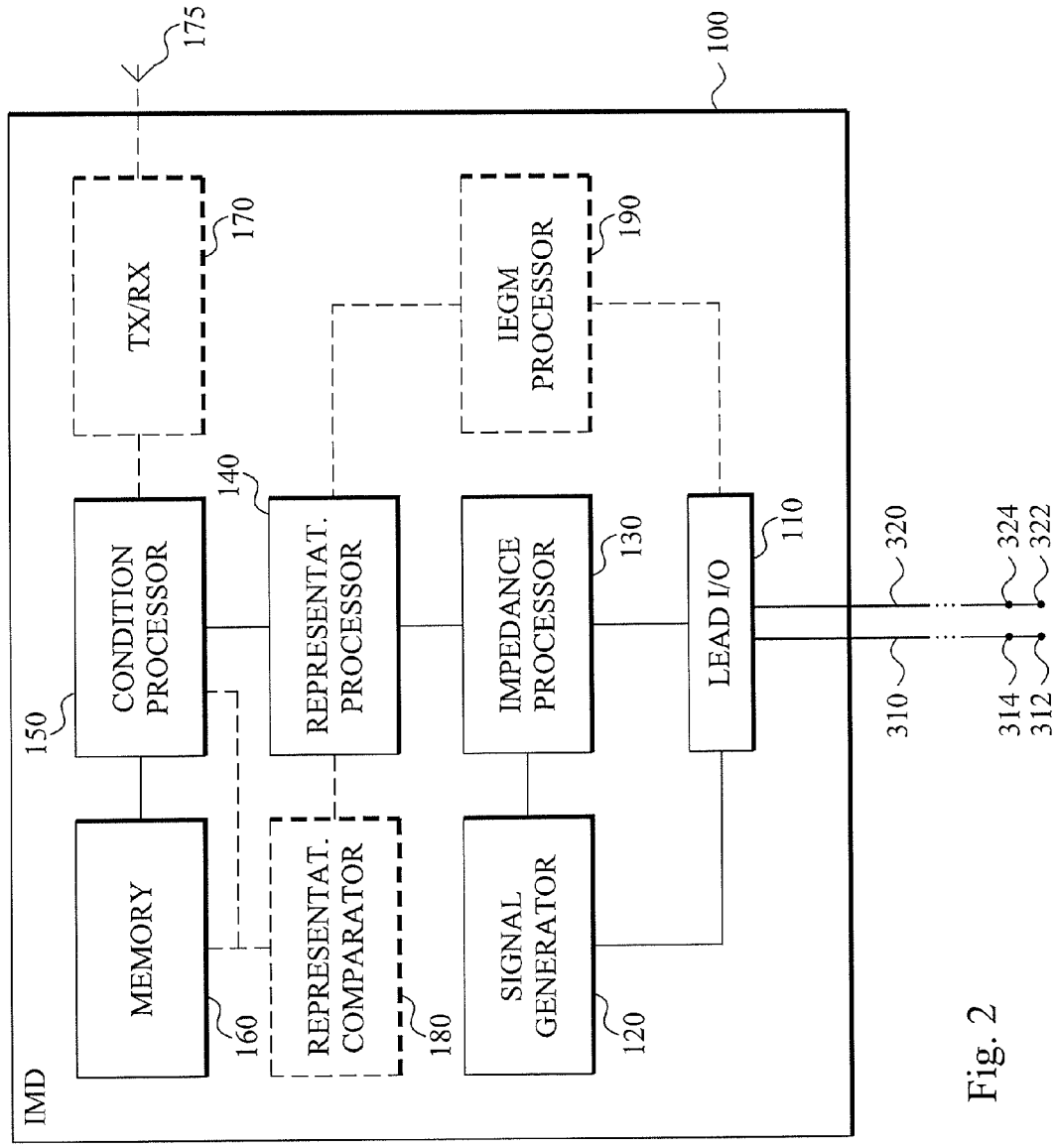
FIG. 2 is a schematic block diagram of an embodiment of an implantable medical device.

FIG. 2 is a schematic block diagram of an IMD 100 according to an embodiment. The IMD 100 comprises a lead connecting arrangement 110 represented as a lead input/output (I/O) 110 in FIG. 2. This lead I/O 110 is, in operation, connectable to multiple cardiac leads 310, 320, each having at least one electrode 312, 314, 322, 324 used for applying and sensing electric signals to and from the cardiac tissue of a subject. As is well known in the art, such an implantable lead or catheter 310, 320 has a proximal end connectable to the IMD 100 through the lead I/O 110. This IMD-connecting end presents one or more electric terminals that are in electric connection with the electrodes 312, 314, 322, 324 present on the opposite distal lead end, where the electric connection is achieved by electric conductors running along the length of the lead body. The distal lead end with its electrodes 312, 314, 322, 324 is then provided in connection with the heart tissue. For this purpose, the lead 310, 320 can include a tissue anchoring element, such as a helical fixation element, though other fixation elements, such as passive fixation elements, including fins, tines, etc., are also common. The fixation element can indeed constitute one of the electrodes of the lead 310, 320, while remaining electrodes can be ring electrodes, also denoted indifferent electrodes, defibrillation electrode, or the like.

The IMD 100 is connected to multiple, i.e. at least two, implantable cardiac leads 310, 320. The cardiac leads 310, 320 can be intracardiac leads positioned in any of the chambers of the heart, such as right and/or left atrium and/or ventricle. Alternatively, the leads 310, 320 could be epicardially positioned relative the heart, such as in the coronary vein. Also a combination of endocardial and epicardial leads is contemplated by the present invention. In a preferred embodiment, the IMD 100 and the lead I/O 110 are connected to a ventricular lead 310, such as right ventricular lead and/or coronary vein lead (left ventricular lead), and an atrial lead 320, such a right atrial lead and/or a left atrial lead.

A signal generator 120 of the IMD 100 is electrically connected to the lead I/O 110 and electrodes 312, 314, 322, 334 of the connectable cardiac leads 310, 320. The generator 120 generates a first electric signal and a second electric signal. The second electric signal may be the same as or different from the first electric signal. The electric signals are alternating current (AC) signals having particular frequencies. The first electric signal is applicable over at least a portion of an atrium of a first side of a heart in a subject by two electrodes 312, 314 of the multiple connectable electrodes 312, 314, 322, 324. Correspondingly, the second electric signal is applicable over at least a portion of a ventricle of the first side of the heart by two of the connectable electrodes 322, 324. These two electrodes 322, 324 are typically different from or at least one of them is different from the electrodes 312, 314 used for applying the first electric signal.

The two electric signals are applied by the electrodes 312, 314, 322, 324 to the same side of the heart, either in parallel or preferably, in order to reduce any interference therebetween, sequentially. Thus, the two electric signals can be applied to the right side of the heart or to the left side of the heart. In order to provide a complete monitoring of both the left and the right side of the heart, the first electric signal can first be applied to the right atrium and then the left atrium, or vice versa. Alternatively, a third electric signal generated by the signal generator 120 is applied over at least a portion of the left atrium if the first electric signal is applied over the right atrium. Correspondingly, the second electric signal can be applied to both the right and left ventricle or a fourth electric signal generated by the signal generator 120 is applied over at least a portion of the left ventricle if the second electric signal is applied over at least a portion of the right ventricle.

In operation, the signal generator 120 generates the electric signals having defined time-dependent voltage/current profiles and forwards the signals to the lead I/O 110. The lead I/O 110 directs the electric signals to the two relevant signal applying electrodes to apply the signals over respective portions, i.e. right atrium, right ventricle and/or left atrium, left ventricle, of the heart.

Two electrodes 312, 314 of the multiple connected electrodes 312, 314, 322, 324 collect a first resulting electric signal, i.e. first resulting AC signal, originating from at least the portion of the atrium. This first resulting signal is due to the applied first electric signal from the signal generator 120. A second resulting electric signal is likewise collected by two of the electrodes 322, 324 but over at least a portion of the ventricle of the same side of the heart as where the first resulting electric signal was measured. In a preferred implementation, the collected first and second resulting electric signals are sensed AC signals.

An impedance processor 130 is electrically connected to the signal generator 120 and the lead I/O 110. The impedance processor 130 processes the first electric signal generated by the signal generator 120 and the first resulting electric signal collected by the two electrodes 312, 314 connected to the lead I/O 110. In more detail, the processor 130 calculates atrial impedance data or signal based on the generated first electric signal, such as based on the current of the first electric signal, and the first resulting electric signals, e.g. based on the measured voltage of the first resulting electric signal. This atrial impedance data is reflective of the cardiogenic impedance of the atrium during at least a sub-phase of at least one heart cycle.

The impedance processor 130 also processes the second electric signal from the signal generator 120 and the second resulting electric signal collected from the ventricle in the heart. The impedance processor 130 uses these two electric signals for determining ventricular impedance data or signal reflective of the cardiogenic impedance of the ventricle during the at least a sub-phase of the at least one heart cycle.

Determination of impedance data based on applied and measured electric signals is well-known in the art and is therefore not further described herein.

The impedance processor 130 can utilize different filter combinations, such as bandpass filters, in order to obtain the desired atrial and ventricular impedance data based on the measured voltage of the resulting electric signals and the current of the applied electric signals. The impedance data determined by the impedance processor 130 can be a complex impedance signal, i.e. comprising a resistive and a reactive component or alternatively an impedance amplitude and phase angle. Alternatively, only the resistive or reactive component or the impedance amplitude is used as impedance data.

The relevant sub-phase of the heart cycle can be the diastolic portion of the heart cycle in a first embodiment. In another embodiment, the relevant sub-phase of the heart cycle is the systolic portion of the heart cycle. Yet another embodiment determines the atrial and ventricular impedance data for substantially the whole heart cycle, i.e. comprising both diastolic and systolic impedance data samples.

In a particular embodiment, the impedance processor 130 can determine the atrial and ventricular impedance data as average impedance data. In such a case, the first and second electric signals are applied over the atrium and the ventricle, respectively, over multiple, preferably consecutive, heart cycles. The first and second resulting electric signals are furthermore measured during multiple heart cycles. The atrial impedance data is then the average atrial impedance during the relevant sub-phase or the whole heart cycle and the ventricular impedance data is the average ventricular impedance during the sub-phase or the whole heart cycle.

A representation processor 140 is implemented in the IMD 100 connected to the impedance processor 130. The representation processor 140 receives the atrial impedance data from the processor 130 or fetches it from a memory 160 included in the IMD 100 in the case the impedance processor 130 has previously stored the data therein. The impedance processor 140 estimates an atrial impedance representation or parameter based on the atrial impedance data. Correspondingly, the ventricular impedance data fetched from the impedance processor 130 or the memory 160 is processed for the purpose of estimating a ventricular impedance representation or parameter. The atrial impedance representation is therefore representative of the cardiogenic impedance of the right or left atrium during diastole and/or during systole of the heart cycle or an average heart cycle. The ventricular impedance representation is instead indicative of the cardiogenic impedance of the right or left ventricle during diastole and/or during systole of the, possibly average, heart cycle.

The determined atrial and ventricular impedance representations are forwarded to a condition processor 150 implemented in the IMD 100. The condition processor 150 uses the input atrial and ventricular impedance representations for determining a condition of a monitored heart valve.

The IMD 100 preferably has access to respective reference atrial and ventricular impedance representations, such as from the memory 160. In such a case, an optional representation comparator 180 compares the atrial impedance representation with the reference atrial impedance representation and compares the ventricular impedance representation with the reference ventricular impedance representation. The condition processor 150 determines the valve condition, such as valve regurgitation or valve stenosis, if there is a significant difference between at least one of the reference impedance representations and the relevant impedance representations. A significant difference is present if the atrial and/or ventricular impedance representation differs from the reference atrial and/or ventricular impedance representation with more that an atrial/ventricular threshold value. If no significant differences are detected the condition processor 150 determines a normal valve condition or operation.

The reference impedance representations present in the memory 160 can be pre-defined atrial and ventricular impedance representations indicative of normal and correct valve function. Alternatively and preferably, the reference atrial and ventricular impedance representations have previously been determined by the IMD 100 to thereby get IMD- and patient-specific reference impedance representations. In such a case, the reference impedance representations are basically determined in the same way as the atrial and ventricular impedance representations, i.e. involving the operation of the signal generator 120, the impedance processor 130 and the representation processor 140 as previously described.

The reference impedance representations are then preferably generated during a period of time when it is confirmed that no valve regurgitation, stenosis or other negative medical condition is present. This can be confirmed by the patient's physician, e.g. at a patient follow-up and/or IMD status check visit.

If the condition processor 150 concludes the presence of a tentative deleterious valve condition in at least one of the monitored heart valves, diagnostic data representative of the heart condition is generated. This data can be entered in the memory 160 for later uploading to an external communication unit. Alternatively, or in addition, the data can be directly and wirelessly sent to the external unit using the transmitter 170 and connected antenna 175 of the IMD 100. If the IMD 100 has an alarm unit capable of sounding an alarm signal or providing a tactile alarm signal, such unit could run an alarm if the condition processor 150 detects a severe deterioration of valve performance as determined based on an analysis of the atrial and ventricular impedance representations.

In a particular embodiment, the IMD 100 determines at least four impedance representations and uses all these or at least a subset of them in the heart valve monitoring.

The impedance processor 130, thus, is preferably arranged for determining atrial impedance data based on the first electric signal applied by the signal generator 120 and the first resulting electric signal from the lead I/O 110. This atrial impedance data is indicative of the cardiogenic impedance of the right or left atrium during both a diastolic phase and a systolic phase of one or multiple heart cycles. The impedance processor 130 also determines ventricular impedance data based on the second electric signal applied by the signal generator 120 and the second resulting electric signal from the lead I/O 110. The ventricular impedance data is representative of the cardiogenic impedance of the right or left ventricle during the diastolic and systolic phases of one or multiple heart cycles.

The atrial and ventricular impedance data is forwarded to the representation processor 140 for further processing. The representation processor 140 identifies those atrial and ventricular impedance data samples corresponding to diastole and those that corresponds to systole. This sorting of data samples can be conducted solely based on the impedance data itself. In other words, the sorting of data samples can be based on the change in impedance values in the atrium or ventricle naturally occurs in diastole and systole. Thus, the respective well-known morphologies in the cardiogenic impedance over a heart cycle are used to identify the start and end of diastole and systole.

In an alternative approach the IMD 100 comprises an electrogram or IEGM processor 190 for recording an intracardiac electrogram (IEGM) of the heart during the at least one heart cycle over which impedance data samples are determined. This IEGM processor 190 basically receives electric signals collected by electrodes 312, 314, 322, 324 of the cardiac leads 310, 320 and originating from the heart. The sampling frequency of this IEGM data is preferably the same or has at least a well-defined relationship to the sampling frequency of the impedance data. The diastolic and systolic phases of the heart cycle or cycles are typically identified from the IEGM data in a manner well known in the art. The start and end of diastole and systole are identified and impedance data samples coinciding with the start and end of diastole and systole are identified by the representation processor 140 using the pre-defined relationship between sampling frequencies.

The representation processor 140 can therefore sort the impedance data samples from the impedance processor 130 into atrial and ventricular diastolic and systolic impedance data samples, respectively, based on the IEGM data from the IEGM processor 190.

The representation processor 140 estimates a diastolic, atrial impedance representation $(Z_A^D)$ based on the atrial impedance data samples coinciding with the diastolic phase of the heart cycle or the average heart cycle. A systolic, atrial impedance representation $(Z_A^S)$ is also determined based on the atrial impedance data samples from the systolic phase. Corresponding ventricular representations, i.e. a diastolic, ventricular impedance representation ($Z_V^D$) and a systolic, ventricular impedance representation ($Z_V^S$), are also determined but based on the diastolic and systolic ventricular impedance data samples, respectively. All these impedance representations are furthermore generated from a same side of the heart. Thus, the impedance representations can be reflective of the atrial and ventricular impedance during diastole and systole of the right side of the heart, $Z_{RA}^D$, $Z_{RA}^S$, $Z_{RV}^D$, $Z_{RV}^S$, or the left side of the heart, $Z_{LA}^D$, $Z_{LA}^S$, $Z_{LV}^D$, $Z_{LV}^S$. Alternatively, both sides of the heart are monitored, giving a preferred total of eight impedance representations, $Z_{RA}^D$, $Z_{RA}^S$, $Z_{RV}^D$, $Z_{RV}^S$, $Z_{LA}^D$, $Z_{LA}^S$, $Z_{LV}^D$, $Z_{LV}^S$.

The condition processor 150 uses the determined diastolic and systolic atrial and ventricular impedance representations for determining the presence of any negative heart valve condition.

The units 110 to 190 of the IMD 100 can be implemented in hardware, software of a combination of hardware and software.

As was mentioned in the foregoing, the respective impedance representation is preferably compared to a respective reference impedance representation. The resulting difference is compared to a threshold value and if exceeding the threshold value, the IMD 100 indicates that a heart valve condition has been determined. In such implementations, the representation comparator 180 calculates the differences between the impedance representations and the reference impedance representations:

$$\Delta Z_A^D = Z_A^D - RZ_A^D$$

$$\Delta Z_A^S = Z_A^S - RZ_A^S$$

$$\Delta Z_V^D = Z_V^D - RZ_V^D$$

$$\Delta Z_V^S = Z_V^S - RV_V^S$$

The condition processor 150 compares these differences with respective threshold values, which may be the same or different, $T_A^D$, $T_A^S$, $T_V^D$, $T_V^S$.

In the following, the embodiments are disclosed further in connection with determination of particular valve conditions and for specific heart valves.

Stenosis of Mitral Valve, Tricuspid Valve

The mitral and tricuspid valves are positioned between the atriums and the ventricles in the heart, with the mitral valve between the left atrium and ventricle and the tricuspid valve between the right atrium and ventricle.

The condition processor 150 of the IMD 100 determines a tentative stenosis condition of the mitral and/or tricuspid valve if the difference between the diastolic, atrial impedance representation and the reference diastolic, atrial impedance representation exceeds the diastolic, atrial threshold value and if the difference between the diastolic, ventricular impedance representation and the reference diastolic, ventricular impedance representation exceeds the diastolic, ventricular threshold value.

In other words the condition processor 150 determines the presence of mitral valve stenosis if: $\Delta Z_{LA}^D = Z_{LA}^D - RZ_{LA}^D > T_{LA}^D$ and $\Delta Z_{LV}^D = Z_{LV}^D - RZ_{LV}^D > T_{LV}^D$. Tricuspid valve stenosis is, correspondingly, determined if $\Delta Z_{RA}^D = Z_{RA}^D - RZ_{RA}^D > T_{RA}^D$ and $\Delta Z_{RV}^D = Z_{RV}^D - RZ_{RV}^D > T_{RV}^D$.

In mitral/tricuspid valve stenosis, the kinetics of the heart valve is impaired as the opening of the valve becomes impeded by the stenosis condition. Abnormal opening of the mitral/tricuspid valve during diastole when blood is to flow and be pumped from the left/right atrium to the ventricle will affect the blood flow in atrium and ventricle during diastole.

Without being bound by theory, the insufficient opening of the mitral/tricuspid valve during stenosis slows down the filling of the left/right ventricle with blood from the atrium. This in turn implies that the decrease in ventricular impedance occurring due to the increasing blood volume in the ventricles during diastole will be slower, i.e.

$$\frac{dZ_V^D}{dt}$$

decreases. Furthermore, the increase in atrial impedance occurring due the decreasing blood volume in the atriums during diastole will also be slower, i.e.

$$\frac{dZ_A^D}{dt}$$

decreases.

In addition to these volume-related effects that are seen in the diastolic, atrial and ventricular impedance representations, the stenosis condition will also give rise to other effects that are detected through impedance measurements.

In normal valve function, blood is emptied and filled in a continuous manner with minimum energy consumption. The filling of blood in the ventricles causes a blood swirl flow, in which the blood is constantly flowing, moving and rotating.

In the case of AV plane valve stenosis (mitral or tricuspid valve), the valve is unable to fully open during diastole, making it more difficult for the atrium in question to perform adequate atrial transport of blood to the ventricle. The blood filling pattern to the ventricle is therefore changed. In normal atrial function, the atrium contractility will increase creating an increased peak blood velocity through the AV plane to ensure adequate ventricular filling. This will alter the ventricular filling blood flow pattern, i.e. in total disrupting the normal blood swirl flow in the atrium and the ventricle during diastole.

This means that an incorrect opening of the mitral/tricuspid valve will cause another blood emptying pattern in the atriums and another blood filling pattern in the ventricles. Thus, the swirl flow of leaving blood in the atriums and newly arriving blood in the ventricles will be different as compared to a normal situation with fully opened valves. This means that new vortices and whirlpools normally not present in the atriums and ventricles now occurs as the blood must take a somewhat different path when leaving the atriums and entering the ventricles as the valves are not fully opened. Such localized phenomena in the blood in the atriums and the ventricles will be identifiable in the impedance data collected in these heart chambers.

Mitral and tricuspid valve stenosis does not lead to any significant changes in atrial and ventricular impedance during systole if the stenotic valve can be fully closed during systole.

Figure 4:
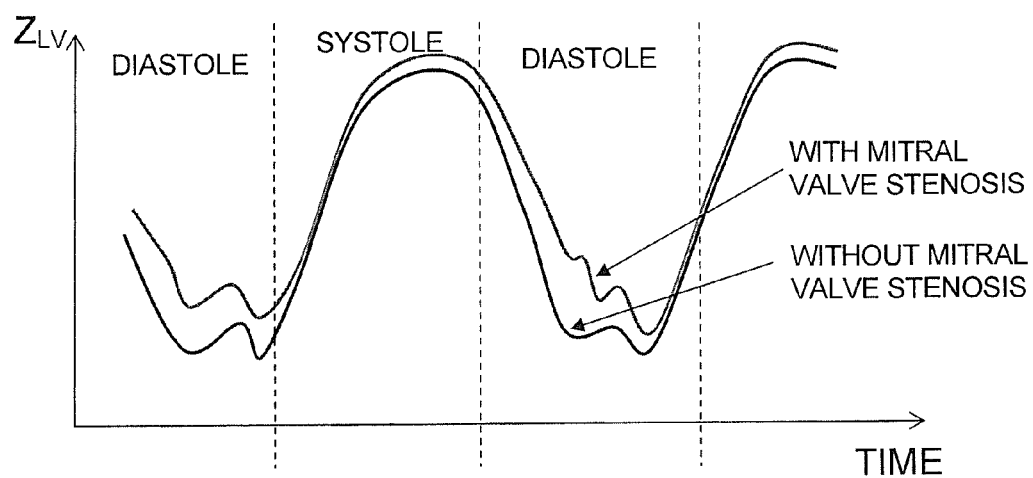
FIG. 4 is a diagram schematically illustrating a change in determined left ventricular impedance occurring during diastole in the case of mitral valve stenosis.

FIG. 4 is a schematic illustration of a left ventricular impedance representation recorded for one and a half heart cycle with a mitral valve stenosis. The corresponding reference left ventricular impedance representation, i.e. without any mitral valve stenosis, is also indicated. As is seen in the figure, there is a significant difference in the left ventricular impedance during diastole but only a slight change due to the stenosis in systole.

Mitral Valve, Tricuspid Valve Regurgitation

The condition processor 150 of the IMD 100 determines a tentative regurgitation condition of the mitral and/or tricuspid valve if the difference between the systolic, atrial impedance representation and the reference systolic, atrial impedance representation exceeds the systolic, atrial threshold value but the difference between the systolic, ventricular impedance representation and the reference systolic, ventricular impedance representation does not exceed the systolic, ventricular threshold value.

In other words the condition processor 150 determines the presence of mitral valve regurgitation if: $\Delta Z_{LA}^S = Z_{LA}^S - RZ_{LA}^S > T_{LA}^S$ and $\Delta Z_{LV}^S = Z_{LV}^S - RZ_{LV}^S \leq T_{LV}^S$. Tricuspid valve regurgitation is, correspondingly, determined if $\Delta Z_{RA}^S = Z_{RA}^S - RZ_{RA}^S > T_{RA}^S$ and $\Delta Z_{RV}^S = Z_{RV}^S - RZ_{RV}^S \leq T_{RV}^S$.

In mitral/tricuspid regurgitation the heart valve cannot fully close, thereby causing a backflow of blood from the left/right ventricle to the atrium during systole.

Without being bound by theory, the lack of fully closed valve during systole causes blood to flow from the ventricle back into the atrium as the ventricle contracts. Thus, the systolic, atrial impedance will decrease as a consequence of the arriving blood. The passive filling of the atria during systole is therefore changed because of the systolic pumping action of blood flowing back up into the atrium. The normal blood swirl flow will be disrupted in the atrium during systole and localized effects in the blood as it enters the atrium, such as whirlpools and vortices will be noticeable in the systolic, atrial impedance.

In clear contrast, the systolic, ventricular impedance will not be or will only be marginally affected by the mitral/tricuspid valve regurgitation. Correspondingly, it is not expected that any significant, detectable characteristics in the diastolic, atrial or ventricular impedance will be present due to the valve regurgitation.

Figure 5:
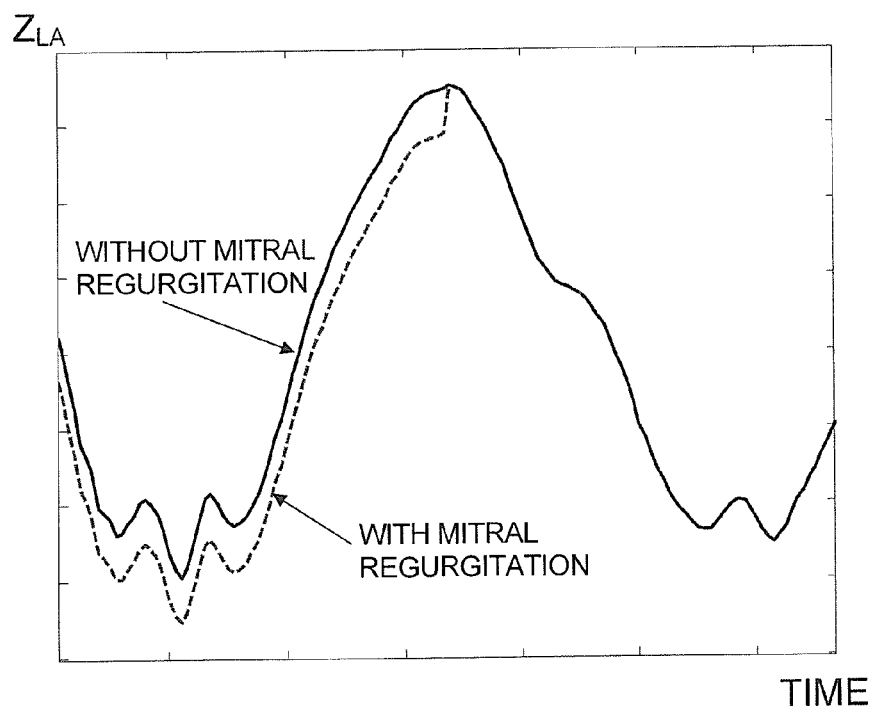
FIG. 5 is a diagram schematically illustrating a change in determined left atrial impedance occurring during systole in the case of mitral valve regurgitation.

FIG. 5 illustrates the left atrial impedance recorded during a heart cycle. The unbroken line represents the atrial impedance without any heart valve malfunction. The hatched line indicates the left atrial impedance for mitral valve regurgitation. The change in left atrial impedance is mainly seen during systole, while the diastolic, atrial impedance changes only marginally with mitral valve regurgitation.

Stenosis of Aortic Valve, Pulmonary Valve

The aortic and pulmonary valves are positioned between the ventricles and arteries connected to ventricles and provided for transporting blood exiting the ventricles throughout the body, i.e. the systemic circulation system, or to the lungs, i.e. the pulmonary circulation system. The aortic valve is arranged between the left ventricle and the aorta, while the pulmonary valve is provided between the right ventricle and the pulmonary artery.

The condition processor 150 of the IMD 100 determines a tentative stenosis condition of the aortic and/or pulmonary valve if the difference between the systolic, atrial impedance representation and the reference systolic, atrial impedance representation does not exceed the systolic, atrial threshold value but the difference between the systolic, ventricular impedance representation and the reference systolic, ventricular impedance representation exceeds the systolic, ventricular threshold value.

In other words the condition processor 150 determines the presence of aortic valve stenosis if: $\Delta Z_{LA}^S = Z_{LA}^S - RZ_{LA}^S \leq T_{LA}^S$ and $\Delta Z_{LV}^S = Z_{LV}^S - RZ_{LV}^S > T_{LV}^S$. Pulmonary valve stenosis is, correspondingly, determined if $\Delta Z_{RA}^S = Z_{RA}^S - RZ_{RA}^S \leq T_{RA}^S$ and $\Delta Z_{RV}^S = Z_{RV}^S - RZ_{RV}^S > T_{RV}^S$.

In aortic/pulmonary valve stenosis, the kinetics of the heart valve is impaired as the opening of the valve becomes impeded by the stenosis condition. Abnormal opening of the aortic/pulmonary valve during systole when blood is to flow and be pumped from the left/right ventricle to the connected artery will affect the blood flow in ventricle during systole.

Without being bound by theory, the insufficient opening of the aortic/pulmonary valve during stenosis slows down the emptying of the left/right ventricle of blood. This in turn implies that the increase in ventricular impedance occurring due to the decreasing blood volume in the ventricles during systole will be slower, i.e.

$$\frac{dZ_V^S}{dt}$$

decreases. The systolic ejection pattern of the ventricle is also changed. In normal ventricular function, the ventricular contractility will increase creating an increased peak blood velocity through the aortic and pulmonary valves. However, the stenosis will alter the ventricular blood flow pattern, i.e. disrupting the normal ventricular blood swirl flow during systole. Thus, localized effects in the blood volume in the ventricles, such as whirlpools and vortices, occurring due to the narrowed opening from the ventricle, will also be detectable in the systolic, ventricular impedance.

It is expected that no significant change in the systolic, atrial impedance, or in the diastolic, atrial and ventricular impedance will be detectable during aortic/pulmonary valve stenosis.

Aortic Valve, Pulmonary Valve Regurgitation

The condition processor 150 of the IMD 100 determines a tentative regurgitation condition of the aortic and/or pulmonary valve if the difference between the diastolic, atrial impedance representation and the reference diastolic, atrial impedance representation does not exceed the diastolic, atrial threshold value but the difference between the diastolic, ventricular impedance representation and the reference diastolic, ventricular impedance representation exceeds the diastolic, ventricular threshold value.

In other words the condition processor 150 determines the presence of aortic valve regurgitation if: $\Delta Z_{LA}^D = Z_{LA}^D - RZ_{LA}^D \leq T_{LA}^D$ and $\Delta Z_{LV}^D = Z_{LV}^D - RZ_{LV}^D > T_{LV}^D$. Pulmonary valve regurgitation is, correspondingly, determined if $\Delta Z_{RA}^D = Z_{RA}^D - RZ_{RA}^D \leq T_{RA}^D$ and $\Delta Z_{RV}^D = Z_{RV}^D - RZ_{RV}^D > T_{RV}^D$.

In aortic/pulmonary regurgitation the heart valve cannot fully close, thereby causing a backflow of blood from the systemic/pulmonary circulatory system to the ventricles during diastole.

Without being bound by theory, the lack of fully closed valve during diastole causes blood to flow from the aorta or the pulmonary artery back into the ventricles. Thus, the diastolic, ventricular impedance will decrease as a consequence of the arriving blood. The ventricle connected to the valve in question will have a disrupted filling pattern as the arterial blood flow is flowing back through the valve during diastole. The normal blood swirl flow in the ventricle during diastole will therefore be disrupted. Thus, localized effects in the blood as it enters the ventricle, such as whirlpools and vortices will be noticeable in the diastolic, ventricular impedance.

In clear contrast, the diastolic, atrial impedance will not be or will only be marginally affected by the aortic/pulmonary valve regurgitation. Correspondingly, it is not expected that any significant, detectable characteristics in the systolic atrial and ventricular impedance will be present due to the valve regurgitation.

Table I and II below summaries the expected changes in the impedance representations occurring for different heart valve conditions.

TABLE I

Heart valve conditions on left heart side

| | Diastole | Systole |
|---|---|---|
| $\Delta Z_{LA}$ OK $\Delta Z_{LV}$ OK | — | — |
| $\Delta Z_{LA}$ √ $\Delta Z_{LV}$ OK | — | Mitral valve regurgitation |
| $\Delta Z_{LA}$ OK $\Delta Z_{LV}$ √ | Aortic valve regurgitation | Aortic valve stenosis |
| $\Delta Z_{LA}$ √ $\Delta Z_{LV}$ √ | Mitral valve stenosis | — |

$\Delta Z$ OK indicates no significant difference between the impedance representation and the reference impedance representation;
$\Delta Z$ √ indicates a significant difference between the impedance representation and the reference impedance representation.

TABLE II

Heart valve conditions on right heart side

| | Diastole | Systole |
|---|---|---|
| $\Delta Z_{RA}$ OK $\Delta Z_{RV}$ OK | — | — |
| $\Delta Z_{RA}$ √ $\Delta Z_{RV}$ OK | — | Tricuspid valve regurgitation |
| $\Delta Z_{RA}$ OK $\Delta Z_{RV}$ √ | Pulmonary valve regurgitation | Pulmonary valve stenosis |
| $\Delta Z_{RA}$ √ $\Delta Z_{RV}$ √ | Tricuspid valve stenosis | — |

In the foregoing, the IMD has been described as containing the processing functionalities required for determining the atrial and ventricular impedance data, estimating the atrial and ventricular impedance representations and performing the valve condition determination. FIG. 1 illustrates a system 300 comprising the IMD 100 and a non-implantable communication and processing device 200, exemplified as the programmer or physician's workstation in the figure. The system 300 comprises the previously described impedance processor 230, the representation processor 240 and the condition processor 250. In a first embodiment all these processors are provided in the IMD 100 as illustrated in FIG. 2. The IMD 100 may then communicate the result of the valve condition determination to the receiver 270 of the programmer 200, for instance for display to the physician on the display screen 210.

A second embodiment of the system 300 has the impedance processor and the representation processor arranged in the IMD 100. However, the condition processor 250 is instead arranged in the programmer 200. The IMD 100 therefore determines the atrial and ventricular impedance representations and transmits them to the receiver 270 of the programmer 200. The condition processor 250 uses these impedance representations for determining the condition of a heart valve as previously described.

In a third embodiment of the system 300, the impedance processor is implemented in the IMD 100, while both the representation processor 240 and the condition processor 250 are arranged in the programmer 200. The impedance data determined by the impedance processor is therefore uploaded to the receiver 270 of the programmer 200 for being input to the representation processor 240.

Finally, a fourth embodiment of the system 300 has the impedance processor 230, representation processor 240 and the condition processor 250 implemented in the programmer 200. The IMD 100 therefore merely collects the raw electric signal and transmits the relevant voltage and current data to the programmer 200 for calculation of the atrial and ventricular impedance data in the impedance processor 230.

Thus, the processors of the embodiments can be implemented in the IMD 100 or in a non-implantable communication and processing device 200. The operation of the processors is basically the same regardless of implementation site. Correspondingly, the representation comparator of FIG. 2 may instead be provided in the programmer 200 in particular if the condition processor 250 is found in the programmer 200. Correspondingly, the IEGM processor may be found in the programmer 200, especially if the representation processor 240 and the condition processor 250 are arranged in the programmer 200.

The programmer 200 may also contain data memory in similarity to the IMD 100.

If the majority of the processors are provided in the IMD, more of the data processing is of course performed in the IMD. However, the amount of data sent to the programmer can be kept fairly small, i.e. merely indicating that a heart valve malfunction has been detected, which valve that has been effected (can be managed by a 2-bit valve identifier) and possibly what type of malfunction that has been detected (can be managed by a 2-bit condition identifier in the case of normal, stenosis and regurgitation condition). If the processors instead are provided in the non-implantable device, the processing of the data is performed therein. The IMD must then, though, transmit fairly large amount of raw data to be used by the processors.

Different impedance vectors can generally be used depending on the particular cardiac leads connectable to the IMD. FIGS. 3A to 3D illustrates different such examples of impedance vectors that advantageously can be used in order to determine the aortic and ventricular impedance data used by the invention for the valve condition determination.

FIG. 3A is a schematic illustration of a heart 10, in which a right atrial lead 310 and a coronary vein lead or coronary sinus lead 330 are implanted. Left atrial impedance data can be determined based on bipolar, tripolar or quadropolar measurements using one or two electrodes 312, 314 of the right atrial lead 310 and one or two electrodes 332, 334 of the coronary vein lead 330. In bipolar measurements, one of the right atrial lead electrodes 312, 314 and one of the electrodes 332, 334 of the coronary vein lead 330 are used for both applying the first electric signal and for collecting the first resulting electric signal. In tripolar measurement, one of the electrodes 312, 314, 332, 334, either at the right atrial lead 310 or at the coronary vein lead 330, is used for both signal application and signal collection while remaining two electrodes are dedicated for signal application and signal collection, respectively. Quadropolar measurements uses a pair of signal applying electrodes 312, 332 on the two cardiac leads 310, 330 and another pair of signal collecting electrodes 314, 334 on the cardiac leads 310, 330.

The left ventricular impedance data is in this embodiment determined from bipolar impedance measurements using two of the electrodes 332, 334 of the coronary vein lead 330.

FIG. 3B illustrates an alternative set-up using a so-called multi-electrode coronary vein lead or coronary sinus lead 330. The determination of the left atrial impedance is performed basically in the same way as in FIG. 3A using bipolar, tripolar or quadropolar measurements. Since the coronary sinus lead 330 in this case has access to more than two electrodes 332-338, also tripolar and quadropolar measurements can be used for the left ventricular impedance.

Figure 3D:
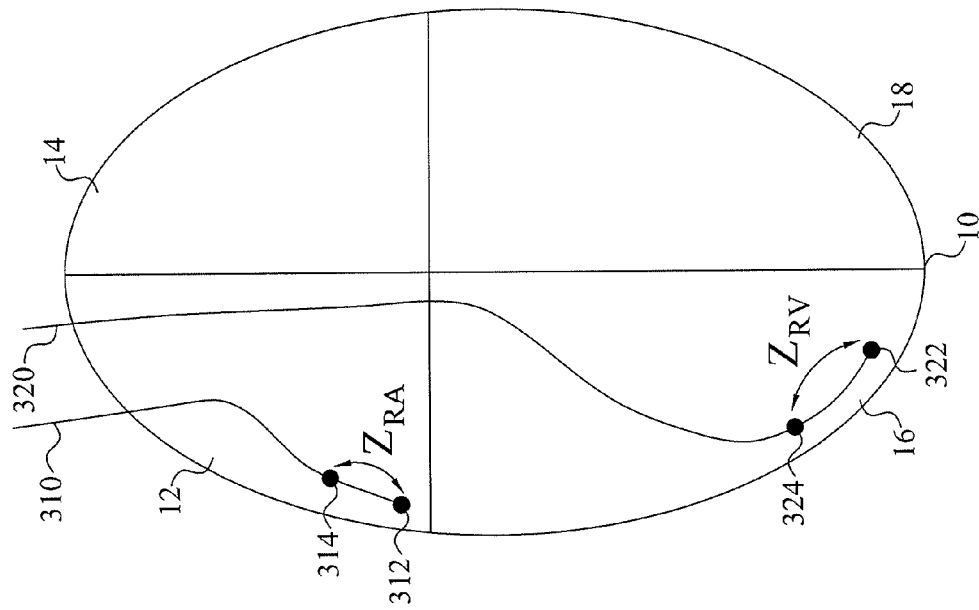
Figure 3C:
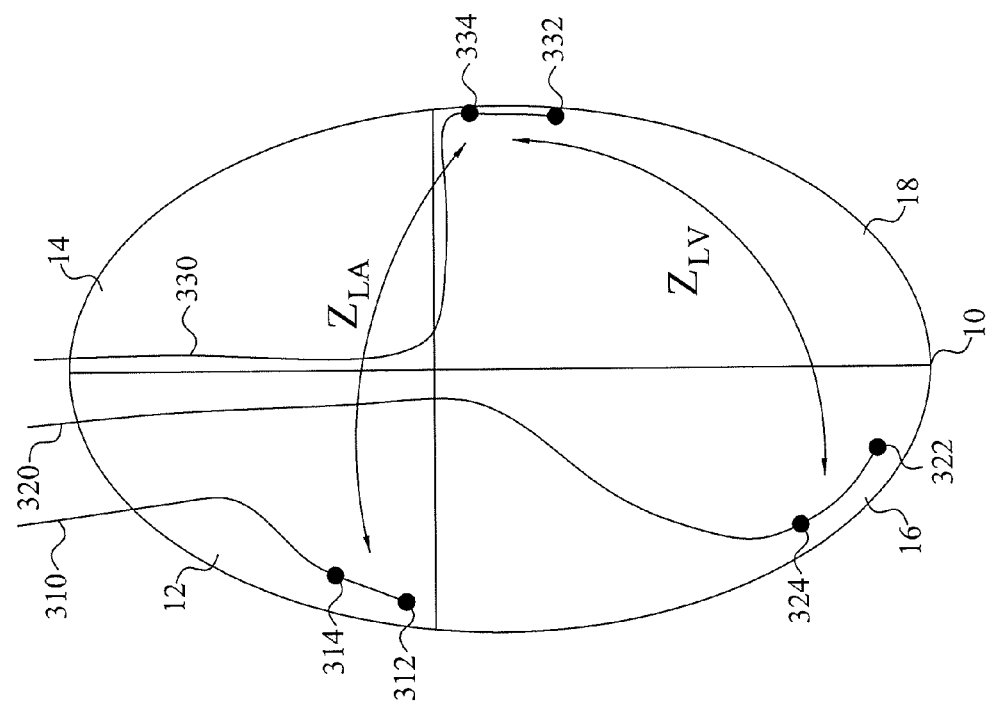

FIG. 3C illustrates yet another set-up in the case of a heart 10 having a right atrial lead 310, a right ventricular lead 320 and a coronary vein lead or coronary sinus lead 330. The left atrial impedance data is preferably determined as discussed in connection with FIG. 3A. In this embodiment, the left ventricular impedance data is determined using bipolar, tripolar or quadropolar measurements using one or two electrodes 322, 324 of the right ventricular lead 320 and one or two electrodes 332, 334 of the coronary vein lead 330. This embodiment may also be used in connection with a multi-electrode lead positioned in the coronary vein as was illustrated in FIG. 3B.

FIG. 3D illustrates a possible set-up of right atrial lead 310 and right ventricular lead 320 for determining right atrial and right ventricular impedance data. In this embodiment, bipolar measurements between the two electrodes 312, 314 of the right atrial lead 310 are used for the right atrial impedance data and bipolar measurements between the right ventricular lead electrodes 322, 324 gives the right ventricular impedance data. At least one of the atrial 310 and ventricular 320 leads may be replaced by a so-called multi-electrode lead for allowing tripolar or quadropolar impedance measurements in the right atrium 12 and/or the right ventricle 16.

The different lead configurations illustrated in FIGS. 3A to 3D may be combined, in particular when monitoring valve operations at both the left and the right side of the heart 10. The lead configuration in FIG. 3C depicting a right atrial lead 310, a right ventricular, possibly multi-electrode, lead 320 and a, possibly multi-electrode, coronary vein lead 330 can be used for determining both $Z_{LA}$, $Z_{LV}$, $Z_{RA}$, $Z_{RV}$. Today coronary vein leads are typically used instead of left ventricular leads introduced inside the left ventricle. It is currently within the medical field considered safer for the patient not to have any leads present in the left ventricle. However, disregarding any such potential risk, the teachings of the present invention can effectively be applied to a lead configuration where the coronary vein lead is replaced by a left ventricular lead.

Different types of impedance representations can be determined by the representation processor 140 of the IMD 100 according to different embodiments. In a first embodiment, the respective atrial and ventricular impedance waveforms are compared to reference atrial and ventricular impedance waveforms or templates. The comparison can be made by calculating the difference between the determined waveform and the corresponding reference waveform in a sample-by-sample manner. The calculated differences are then added up to get an impedance parameter that is used by the condition processor 150 in determining the presence of any heart valve condition. In such a case, the impedance samples corresponding to diastole and those corresponding to systole are preferably handled separately to thereby get, for each investigated heart side, four impedance parameters, the diastolic, atrial; the diastolic ventricular; the systolic atrial and the systolic ventricular parameters. The respective impedance parameters are compared to predefined threshold values that are either hardcoded in the IMD 100, such as present in the memory 160 or downloaded into the IMD 100 using a receiver 170 with connected antenna 175.

Alternatively, the representation processor 140 calculates one or more impedance characteristics or features from the atrial and ventricular impedance data. A listing of different preferred impedance characteristics follows below. Any one or multiple of these characteristics can be used by the invention:

Average impedance—the average impedance during diastole or systole;
Curvature length—the length of the impedance curve during diastole or systole;
Fractionation—is similar to the curvature length but amplitude normalization in the interval [0, 1] is used;
Systolic slope—identifies the maximum first time derivative in the impedance signal during systole; and
Peak to peak—takes the difference in the maximum and minimum impedance value during diastole or systole.

Other impedance characteristics derivable from the diastolic impedance data and the systolic impedance data could be used instead of or as complement to the above-listed examples.

The calculated impedance characteristics during diastole or systole are compared to corresponding reference impedance characteristics calculated from a reference impedance waveform provided in the memory 160 of the IMD 100. In such a case, the reference impedance waveform is preferably an average waveform determined over multiple heart beats with no indication of any heart valve malfunction.

If the difference exceeds the predefined threshold a tentative heart valve malfunction may be present as described above.

A further possibility is to have the representation processor 140 to calculate the first time derivative of the atrial and ventricular impedance. The first derivatives are plotted versus the respective regular impedance data to form so-called impedance loops. Characteristics of the loops can be determined by the representation processor 140, such as loop area, loop radius, loop angle. Such characteristics can be calculated using the method described in U.S. Pat. No. 5,556,419, the teaching of which is hereby incorporated by reference. Alternatively, morphology comparisons using the calculated loops and corresponding reference loops determined from the reference atrial and ventricular impedance waveform as described in U.S. Pat. No. 5,427,112, the teaching of which is hereby incorporated by reference, can be used.

The actual value or values of the thresholds that are used according to the embodiments can be hardcoded in the IMD at the time of implantation. Alternatively, they are downloaded by the physician following the implantation time, such as at a patient follow-up meeting. The threshold values may be fixed or can be updated, for instance by the physician by downloading new, updated threshold values. This may, for instance, be considered if the IMD has notified that there is a valve malfunction based on the determined impedance data. The physician can then, once he/she has concluded that the IMD has determined such a valve malfunction, perform a more complete investigation of the valve condition, such as using an ultrasound probe. If the physician determines that no valve malfunction is present even though the IMD signals this, it might be due to that the local environment around the signal applying and signal measuring electrodes of the cardiac leads has changed somewhat, such as through the ingrowth of connective tissue. Such a change in local environment will in turn be captured in the impedance data and will affect the determined impedance representations. The physician can therefore update threshold values to compensate for this change in electrode environment.

In an alternative and typically more preferred approach, the IMD itself, possibly following that the physician has concluded that no valve malfunction is present, updates the reference impedance representations based on the latest impedance representation or representations. The reference impedance representation can, for example, be in the form of an average of several different impedance representations determined at different time instances. A weighted average is typically preferred to thereby more heavily weight a more recently determined impedance representation as compared to an outdated impedance representation.

Figure 7:
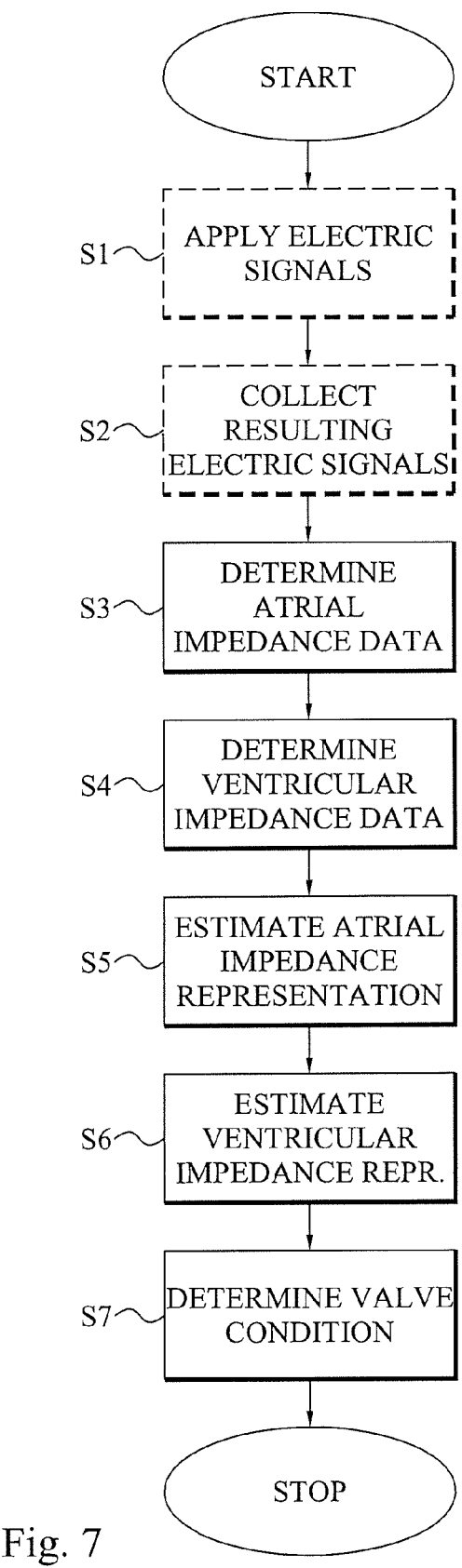
FIG. 7 is a flow diagram illustrating a method of determining a condition of a heart valve.

FIG. 7 is a flow diagram illustrating a method of determining a condition of a valve of a heart in a subject, preferably human subject. The method starts with the optional steps S1 and S2. Step S1 applies a first electric signal, AC signal, over at least a portion of the right and/or left atrium of the heart. A corresponding second electric signal, AC signal, is also applied over at least a portion of the right and/or left ventricle. Resulting electric signals, AC signals, are collected over the right and/or left atrium and ventricle in step S2. Step S3 determines atrial impedance data based on the first applied electric signal, such as based on the current of the first electric signal, and based on the collected first resulting electric signal, such as based on the voltage of the first resulting electric signal. This atrial impedance data is furthermore reflective of the cardiogenic impedance of the atrium during at least a sub-phase, such as diastole and/or systole, of at least one heart cycle.

Ventricular impedance data is determined in step S4 based on the applied second electric signal, such as based on the current of the second electric signal, and based on the collected second resulting electric signal, such as based on the voltage of the second electric signal. The ventricular impedance data is reflective of the cardiogenic impedance of the ventricle during at least the relevant sub-phase.

The two steps S3 and S4 may be conducted serially in the order illustrated in FIG. 7 or in the opposite order. Alternatively, the two steps S3 and S4 are conducted in parallel or at least partly in parallel.

The atrial and ventricular impedance data is preferably determined based on measurements conducted during multiple successive or non-successive heart cycles to thereby obtain average impedance data. This in turn reduces the effect of noise and other disturbances that otherwise may have an impact if the measurements are limited to a single heart cycle. Generally, an average over 5-10 heart cycles often works really well in terms of noise suppression.

The impedance data can represent the atrial and ventricular impedance during diastole, systole or the whole time period of the (average) heart cycle.

A next step S5 estimates an atrial impedance representation based on the atrial impedance data determined in step S3. This atrial impedance representation is a diastolic, atrial impedance representation or a systolic, atrial impedance representation. Alternatively, both diastolic and systolic impedance representations are estimated in step S5.

Step S6 estimates a ventricular impedance representation based on the ventricular impedance data determined in step S4. In similarity to the atrial impedance representation, the ventricular impedance representation could be a diastolic, ventricular impedance representation, a systolic, ventricular impedance representation or both diastolic and systolic ventricular impedance representations are estimated in step S6.

The two steps S5 and S6 may be conducted serially in the order illustrated in FIG. 7 or in the opposite order. Alternatively, the two steps S5 and S6 are conducted in parallel or at least partly in parallel.

The condition of one or more heart valves is determined in step S7 for the purpose of detecting any valve malfunction or confirming normal valve condition. The condition determination is furthermore conducted based on the atrial impedance representation from step S5 and the ventricular impedance representation estimated in step S6.

Steps S1 and S2 are conducted by the IMD. The steps S3 to S7 may be performed in the IMD or may be performed by the programmer.

The procedure illustrated by steps S1 to S7 of FIG. 7 may be conducted once, such as upon a triggering signal generated by the IMD itself or received from an external communication unit, such as programmer. Alternatively, the method is performed periodically or intermittently according to a defined monitoring schedule. Thus, the method can be repeated once per day, once per week, once per month or with some other periodicity.

A particular embodiment of the determining step S3 determines atrial impedance data reflective of the cardiogenic impedance of the atrium during diastole and systole of the heart cycle, of multiple heart cycles or an average heart cycle. Correspondingly, step S4 preferably determines ventricular impedance data indicative of the cardiogenic impedance of the ventricle during diastole and systole.

The estimating steps S5 and S6 use the atrial and ventricular impedance data for generating the previously described diastolic, atrial impedance representation; systolic, atrial impedance representation; diastolic, ventricular impedance representation and systolic, ventricular impedance representation thereby giving a total of four impedance parameters if a single side of the heart is monitored or up to eight impedance parameters if both the right and left heart sides are monitored.

Step S7 uses these estimated impedance representations for determining the condition of the heart valve or preferably of multiple heart valves.

FIG. 8 is a flow diagram illustrating additional steps of the determining method in FIG. 7. The method continues from step S6 of FIG. 7. In these additional steps, the estimated impedance representations are compared with respective reference impedance representations, which have preferably previously been determined during a time period of no valve malfunctions.

Step S10 calculates a difference between the diastolic, atrial impedance representation and the reference diastolic, atrial impedance representation and compares the difference with a diastolic, atrial threshold value. Step S11 correspondingly compares the difference between the systolic, atrial impedance representation and the reference systolic, atrial impedance representation with a systolic, atrial threshold value. The final two steps S12 and S13 perform comparisons between the differences of ventricular impedance representations and the reference ventricular impedance representations and the ventricular threshold values.

These steps S10 to S13 may be performed sequentially in any order or alternatively fully or partly in parallel. The respective threshold values used in the comparisons of step S10 to S13 may all be the same or different. For instance, the threshold values can correspond to a percentage value so that a significant difference in one of the impedance representations is deemed to have occurred if that impedance representation differs with more than the percentage value from its reference impedance representation.

The method continues to step S7 of FIG. 7, where the comparisons are used for determining the presence of any valve malfunction and also what type of valve condition and which heart valve or valves that are effected as described previously and summarized in Tables I and II.

FIG. 9 is a flow diagram illustrating additional steps of the determining method in FIG. 7. The method continues from step S4 of FIG. 7. A next step S20 records an IEGM of the heart, preferably in parallel with the signal measurements used as a basis for determining the atrial and ventricular impedance data. The IEGM is used in step S21 for sorting and classifying the impedance data samples into atrial and ventricular impedance data samples relating to diastole of the heart cycle, the multiple heart cycles or the average heart cycle and those data samples that coincide with systole. The method then continues to step S5, where the atrial and ventricular impedance representations are determined based on the sorted impedance data samples.

The valve condition data generated by embodiments is not necessarily limited to usage as highly valuable diagnostic information to detect any valve condition or any other medical condition that causes symptoms of valve malfunction. IMD implemented for providing cardiac resynchronization therapy (CRT) to patients having dyssynchrony between the left and right ventricles can benefit from embodiments of the invention. When optimizing the CRT parameters of the IMD, valve regurgitation, in particular mitral valve regurgitation, may occur in the case on non-optimal CRT parameters. The valve condition monitoring of embodiments can therefore be used as a complement during CRT parameter, in particular AV time and VV time, optimization by detecting the parameter settings that minimizes or leads to no mitral valve regurgitation.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical device comprising:
   a lead connecting arrangement connectable to multiple cardiac leads each having at least one electrode;
   a signal generator that generates a first electric signal applicable over at least a portion of an atrium of a first side of a heart by a pair of electrodes of said multiple cardiac leads and generating a second electric signal applicable over at least a portion of a ventricle of said first side of the heart by a pair of electrodes among said multiple cardiac leads;
   an impedance processor that determines, based on said first electric signal and a first resulting electric signal measured over at least a portion of the atrium by a pair of electrodes among said multiple cardiac leads, atrial impedance data reflective of a cardiogenic impedance of the atrium during at least a sub-phase of at least one heart cycle and determining, based on said second electric signal and a second resulting electric signal measured over at least a portion of the ventricle by a pair of electrodes among said multiple cardiac leads, ventricular impedance data reflective of a cardiogenic impedance of the ventricle during said at least a sub-phase of said at least one heart cycle;
   a representation processor that estimates an atrial impedance representation based on said atrial impedance data and a ventricular impedance representation based on said ventricular impedance data;
   a condition processor that determines a condition of a valve of the heart based on said atrial impedance representation and said ventricular impedance representation;
   wherein said impedance processor determines, based on said first electric signal and said first resulting electric signal, atrial impedance data a cardiogenic impedance of the atrium during a diastolic phase and a systolic phase of said at least one heart cycle and determining, based on said second electric signal and said second resulting electric signal, ventricular impedance data representing a cardiogenic impedance of the ventricle during said diastolic phase and said systolic phase of said at least one heart cycle;
   wherein said representation processor estimating i) a diastolic, atrial impedance representation based on said atrial impedance data reflective of said cardiogenic impedance of the atrium during said diastolic phase, ii) a systolic, atrial impedance representation based on said atrial impedance data reflective of said cardiogenic impedance of the atrium during said systolic phase, iii) a diastolic, ventricular impedance representation based on said ventricular impedance data reflective of said cardiogenic impedance of the ventricle during said diastolic phase and iv) a systolic, ventricular impedance representation based on said ventricular impedance data reflective of said cardiogenic impedance of the ventricle during said systolic phase; and
   wherein said condition processor is arranged for determining said condition of the valve based on i) said diastolic, atrial impedance representation, ii) said systolic, atrial impedance representation, iii) said diastolic, ventricular impedance representation and iv) said systolic, ventricular impedance representation; and
   a representation comparator that compares i) said diastolic, atrial impedance representation with a reference diastolic, atrial impedance representation, ii) said systolic, atrial impedance representation with a reference systolic, atrial impedance representation, iii) said diastolic, ventricular impedance representation with a reference diastolic, ventricular impedance representation and iv) said systolic, ventricular impedance representation with a reference systolic, ventricular impedance representation, and wherein said condition processor determines said condition of said valve based on said comparisons.

2. The device according to claim 1, wherein the valve is adapted to be located between the atrium and the ventricle and said condition processor determines a tentative stenosis condition of the valve if i) a difference between said diastolic, atrial impedance representation and said reference diastolic, atrial impedance representation exceeds a diastolic, atrial threshold value and ii) a difference between said diastolic, ventricular impedance representation and said reference diastolic, ventricular impedance representation exceeds a diastolic, ventricular threshold value.

3. The device according to claim 1, wherein the valve is adapted to be located between the ventricle and an artery connected to the ventricle and wherein said condition processor determines a tentative stenosis condition of the valve if i) a difference between said systolic, atrial impedance representation and said reference systolic, atrial impedance representation does not exceed a systolic, atrial threshold value but ii) a difference between said systolic, ventricular impedance representation and said reference systolic, ventricular impedance representation exceeds a systolic, ventricular threshold value.

4. The device according to claim 1, wherein the valve is adapted to be located between the atrium and the ventricle and wherein said condition processor determines a tentative regurgitation condition of the valve if i) a difference between said systolic, atrial impedance representation and said reference systolic, atrial impedance representation exceeds a systolic, atrial threshold value but ii) a difference between said systolic, ventricular impedance representation and said reference systolic, ventricular impedance representation does not exceed a systolic, ventricular threshold value.

5. The device according to claim 1, wherein the valve is adapted to be located between the ventricle and an artery connected to the ventricle and wherein said condition processor determines a tentative regurgitation condition of the valve if i) a difference between said diastolic, atrial impedance representation and said reference diastolic, atrial impedance representation does not exceed a diastolic, atrial threshold value but ii) a difference between said diastolic, ventricular impedance representation and said reference diastolic, ventricular impedance representation exceeds a diastolic, ventricular threshold value.

6. An implantable medical device comprising:
a lead connecting arrangement connectable to multiple cardiac leads each having at least one electrode;
a signal generator that generates a first electric signal applicable over at least a portion of an atrium of a first side of a heart by a pair of electrodes of said multiple cardiac leads and generating a second electric signal applicable over at least a portion of a ventricle of said first side of the heart by a pair of electrodes among said multiple cardiac leads;
an impedance processor that determines, based on said first electric signal and a first resulting electric signal measured over at least a portion of the atrium by a pair of electrodes among said multiple cardiac leads, atrial impedance data reflective of a cardiogenic impedance of the atrium during at least a sub-phase of at least one heart cycle and determining, based on said second electric signal and a second resulting electric signal measured over at least a portion of the ventricle by a pair of electrodes among said multiple cardiac leads, ventricular impedance data reflective of a cardiogenic impedance of the ventricle during said at least a sub-phase of said at least one heart cycle;
a representation processor that estimates an atrial impedance representation based on said atrial impedance data and a ventricular impedance representation based on said ventricular impedance data;
a condition processor that determines a condition of a valve of the heart based on said atrial impedance representation and said ventricular impedance representation;
wherein said impedance processor determines, based on said first electric signal and said first resulting electric signal, atrial impedance data a cardiogenic impedance of the atrium during a diastolic phase and a systolic phase of said at least one heart cycle and determining, based on said second electric signal and said second resulting electric signal, ventricular impedance data representing a cardiogenic impedance of the ventricle during said diastolic phase and said systolic phase of said at least one heart cycle;
wherein said representation processor estimating i) a diastolic, atrial impedance representation based on said atrial impedance data reflective of said cardiogenic impedance of the atrium during said diastolic phase, ii) a systolic, atrial impedance representation based on said atrial impedance data reflective of said cardiogenic impedance of the atrium during said systolic phase, iii) a diastolic, ventricular impedance representation based on said ventricular impedance data reflective of said cardiogenic impedance of the ventricle during said diastolic phase and iv) a systolic, ventricular impedance representation based on said ventricular impedance data reflective of said cardiogenic impedance of the ventricle during said systolic phase; and
wherein said condition processor is arranged for determining said condition of the valve based on i) said diastolic, atrial impedance representation, ii) said systolic, atrial impedance representation, iii) said diastolic, ventricular impedance representation and iv) said systolic, ventricular impedance representation; and
an electrogram processor that records an intracardiac electrogram of the heart over said at least one heart cycle, and wherein said representation processor identifies, based on said intracardiac electrogram, i) data samples of said atrial impedance data comprising diastolic, atrial impedance data, ii) data samples of said atrial impedance data comprising systolic, atrial impedance data, iii) data samples of said ventricular impedance data comprising diastolic, ventricular impedance data and iv) data samples of said ventricular impedance data comprising systolic, ventricular impedance data.

7. An implantable medical device comprising:
a lead connecting arrangement connectable to multiple cardiac leads each having at least one electrode;
a signal generator that generates a first electric signal applicable over at least a portion of an atrium of a first side of a heart by a pair of electrodes of said multiple cardiac leads and generating a second electric signal applicable over at least a portion of a ventricle of said first side of the heart by a pair of electrodes among said multiple cardiac leads;
an impedance processor that determines, based on said first electric signal and a first resulting electric signal measured over at least a portion of the atrium by a pair of electrodes among said multiple cardiac leads, atrial impedance data reflective of a cardiogenic impedance of the atrium during at least a sub-phase of at least one heart cycle and determining, based on said second electric signal and a second resulting electric signal measured over at least a portion of the ventricle by a pair of electrodes among said multiple cardiac leads, ventricular impedance data reflective of a cardiogenic impedance of the ventricle during said at least a sub-phase of said at least one heart cycle;
a representation processor that estimates an atrial impedance representation based on said atrial impedance data and a ventricular impedance representation based on said ventricular impedance data;
a condition processor that determines a condition of a valve of the heart based on said atrial impedance representation and said ventricular impedance representation;
wherein said impedance processor determines, based on said first electric signal and said first resulting electric signal, atrial impedance data a cardiogenic impedance of the atrium during a diastolic phase and a systolic phase of said at least one heart cycle and determining, based on said second electric signal and said second resulting electric signal, ventricular impedance data representing a cardiogenic impedance of the ventricle during said diastolic phase and said systolic phase of said at least one heart cycle;
wherein said representation processor estimating i) a diastolic, atrial impedance representation based on said atrial impedance data reflective of said cardiogenic impedance of the atrium during said diastolic phase, ii) a systolic, atrial impedance representation based on said atrial impedance data reflective of said cardiogenic impedance of the atrium during said systolic phase, iii) a diastolic, ventricular impedance representation based on said ventricular impedance data reflective of said cardiogenic impedance of the ventricle during said diastolic phase and iv) a systolic, ventricular impedance representation based on said ventricular impedance data reflective of said cardiogenic impedance of the ventricle during said systolic phase;

wherein said condition processor is arranged for determining said condition of the valve based on i) said diastolic, atrial impedance representation, ii) said systolic, atrial impedance representation, iii) said diastolic, ventricular impedance representation and iv) said systolic, ventricular impedance representation; and wherein said representation processor estimates a diastolic, atrial impedance waveform and a systolic atrial impedance waveform based on said atrial impedance data and a diastolic impedance waveform and a systolic impedance waveform based on said ventricular impedance data.

8. An implantable medical device comprising:
a lead connecting arrangement connectable to multiple cardiac leads each having at least one electrode;
a signal generator that generates a first electric signal applicable over at least a portion of an atrium of a first side of a heart by a pair of electrodes of said multiple cardiac leads and generating a second electric signal applicable over at least a portion of a ventricle of said first side of the heart by a pair of electrodes among said multiple cardiac leads;
an impedance processor that determines, based on said first electric signal and a first resulting electric signal measured over at least a portion of the atrium by a pair of electrodes among said multiple cardiac leads, atrial impedance data reflective of a cardiogenic impedance of the atrium during at least a sub-phase of at least one heart cycle and determining, based on said second electric signal and a second resulting electric signal measured over at least a portion of the ventricle by a pair of electrodes among said multiple cardiac leads, ventricular impedance data reflective of a cardiogenic impedance of the ventricle during said at least a sub-phase of said at least one heart cycle;
a representation processor that estimates an atrial impedance representation based on said atrial impedance data and a ventricular impedance representation based on said ventricular impedance data;
a condition processor that determines a condition of a valve of the heart based on said atrial impedance representation and said ventricular impedance representation;

wherein said impedance processor determines, based on said first electric signal and said first resulting electric signal, atrial impedance data a cardiogenic impedance of the atrium during a diastolic phase and a systolic phase of said at least one heart cycle and determining, based on said second electric signal and said second resulting electric signal, ventricular impedance data representing a cardiogenic impedance of the atrium during said diastolic phase and said systolic phase of said at least one heart cycle;

wherein said representation processor estimating i) a diastolic, atrial impedance representation based on said atrial impedance data reflective of said cardiogenic impedance of the atrium during said diastolic phase, ii) a systolic, atrial impedance representation based on said atrial impedance data reflective of said cardiogenic impedance of the atrium during said systolic phase, iii) a diastolic, ventricular impedance representation based on said ventricular impedance data reflective of said cardiogenic impedance of the ventricle during said diastolic phase and iv) a systolic, ventricular impedance representation based on said ventricular impedance data reflective of said cardiogenic impedance of the ventricle during said systolic phase;

wherein said condition processor is arranged for determining said condition of the valve based on i) said diastolic, atrial impedance representation, ii) said systolic, atrial impedance representation, iii) said diastolic, ventricular impedance representation and iv) said systolic, ventricular impedance representation; and wherein said representation processor generates a diastolic, atrial loop representation and a systolic, atrial loop representation based on said atrial impedance data and a first time derivative of said atrial impedance data and a diastolic, ventricular loop representation and a systolic, ventricular loop representation based on said ventricular impedance data and a first time derivative of said impedance data.

* * * * *